United States Patent
Michos et al.

(10) Patent No.: US 10,525,290 B2
(45) Date of Patent: *Jan. 7, 2020

(54) COMPOSITIONS FOR FORMING FILMS HAVING A DESIRED DEGREE OF OBSCURATION AND METHODS OF MAKING AND USING THE SAME

(75) Inventors: Demetrius Michos, Clarksville, MD (US); James Neil Pryor, West Friendship, MD (US)

(73) Assignee: W. R. Grace & Co.-Conn., Columbia, MD (US)

( * ) Notice: Subject to any disclaimer, the term of this patent is extended or adjusted under 35 U.S.C. 154(b) by 868 days.

This patent is subject to a terminal disclaimer.

(21) Appl. No.: 13/519,736

(22) PCT Filed: Dec. 14, 2010

(86) PCT No.: PCT/US2010/060206
§ 371 (c)(1),
(2), (4) Date: Jun. 29, 2012

(87) PCT Pub. No.: WO2011/081905
PCT Pub. Date: Jul. 7, 2011

(65) Prior Publication Data
US 2012/0288545 A1 Nov. 15, 2012

Related U.S. Application Data

(60) Provisional application No. 61/290,772, filed on Dec. 29, 2009, provisional application No. 61/316,587, filed on Mar. 23, 2010.

(51) Int. Cl.
| | | |
|---|---|---|
| *A61K 8/25* | (2006.01) | |
| *A61Q 19/00* | (2006.01) | |
| *A61K 8/00* | (2006.01) | |
| *A61K 8/26* | (2006.01) | |
| *A61Q 19/08* | (2006.01) | |
| *A61K 8/31* | (2006.01) | |
| *A61K 8/81* | (2006.01) | |
| *A61K 8/891* | (2006.01) | |
| *A61K 8/894* | (2006.01) | |

(52) U.S. Cl.
CPC ............... *A61Q 19/08* (2013.01); *A61K 8/25* (2013.01); *A61K 8/31* (2013.01); *A61K 8/8129* (2013.01); *A61K 8/891* (2013.01); *A61K 8/894* (2013.01); *A61Q 19/00* (2013.01)

(58) Field of Classification Search
None
See application file for complete search history.

(56) References Cited

U.S. PATENT DOCUMENTS

| 2,786,042 A | 3/1957 | Iler .................................. 260/37 |
| 2,801,185 A | 7/1957 | Iler .................................. 106/286 |
| 3,657,680 A | 4/1972 | Stegina et al. ................. 337/308 |
| 3,924,032 A | 12/1975 | Hertl ............................ 427/220 |
| 4,157,920 A | 6/1979 | Wason et al. .................. 106/292 |
| 5,030,286 A | 7/1991 | Crawford et al. ............ 106/435 |
| 5,069,897 A * | 12/1991 | Orr .................................. 424/66 |
| 5,223,559 A | 6/1993 | Arraudeau et al. ............. 524/47 |
| 6,197,384 B1 | 3/2001 | Schbert et al. ................ 427/419 |
| 6,333,053 B1 | 12/2001 | Simon ........................... 424/469 |
| 6,344,240 B1 | 2/2002 | Menon et al. ................. 427/220 |
| 6,380,265 B1 | 4/2002 | Pryor et al. ...................... 516/85 |
| 7,037,475 B2 | 5/2006 | Dokter et al. ................. 423/335 |
| 2002/0141957 A1 | 10/2002 | Tan et al. .......................... 424/63 |
| 2003/0114572 A1* | 6/2003 | Travkina ................. A61K 8/042 524/492 |
| 2003/0131536 A1* | 7/2003 | Kostinko .................. A61K 8/25 51/308 |
| 2005/0031658 A1* | 2/2005 | Girier Dufournier et al. ............. 424/401 |
| 2005/0129638 A1 | 6/2005 | Dumousseaux ................ 424/63 |
| 2005/0260147 A1 | 11/2005 | Elliott et al. ..................... 424/63 |
| 2006/0210513 A1* | 9/2006 | Luizzi .................. A61K 8/4913 424/70.13 |
| 2008/0152680 A1 | 6/2008 | Brown et al. ................. 424/401 |
| 2008/0248071 A1 | 10/2008 | Doat et al. .................... 424/401 |
| 2009/0175915 A1 | 7/2009 | Maitra et al. ................. 424/401 |
| 2012/0288546 A1* | 11/2012 | Michos et al. ................ 424/401 |

FOREIGN PATENT DOCUMENTS

| EP | 0658523 | 6/1995 | .............. C23D 5/04 |
| WO | WO 2008022836 A1 * | 2/2008 | ........... C01B 33/183 |

OTHER PUBLICATIONS

Cab-o-sil HS-5 Technical Datasheet, obtained online at: http://adhesives.specialchem.com/product/a-cabot-cab-o-sil-hs-5, downloaded on Jul. 2, 2015, 1 page.*
Sun et al., J. Cosmet. Sci., 2005, 56, 253-265.*
Wason, J. Soc. Cosmet. Chem., 1978, 29, 497-521.*
Chiao et al., Analytical Chem, 1957, 29(11), 1678-1681.*
Cosmetics & Toiletries—Quantification of the Soft-Focus Effect Measuring Light-Diffusing Characteristics of Cosmetic Pigments and Powders—Jul. 1996 by: Dr. Red Emmert, PhD, Rona/EM Industries, Hawthorne, NY, USA.

* cited by examiner

*Primary Examiner* — Abigail Vanhorn

(57) ABSTRACT

Compositions suitable for use as skin care products (e.g., skin cream) are disclosed. Methods of making and using compositions suitable for use as skin care products are also disclosed.

19 Claims, 6 Drawing Sheets

Smooth Continuous Film

Rough Continuous Film

Discontinuous Film

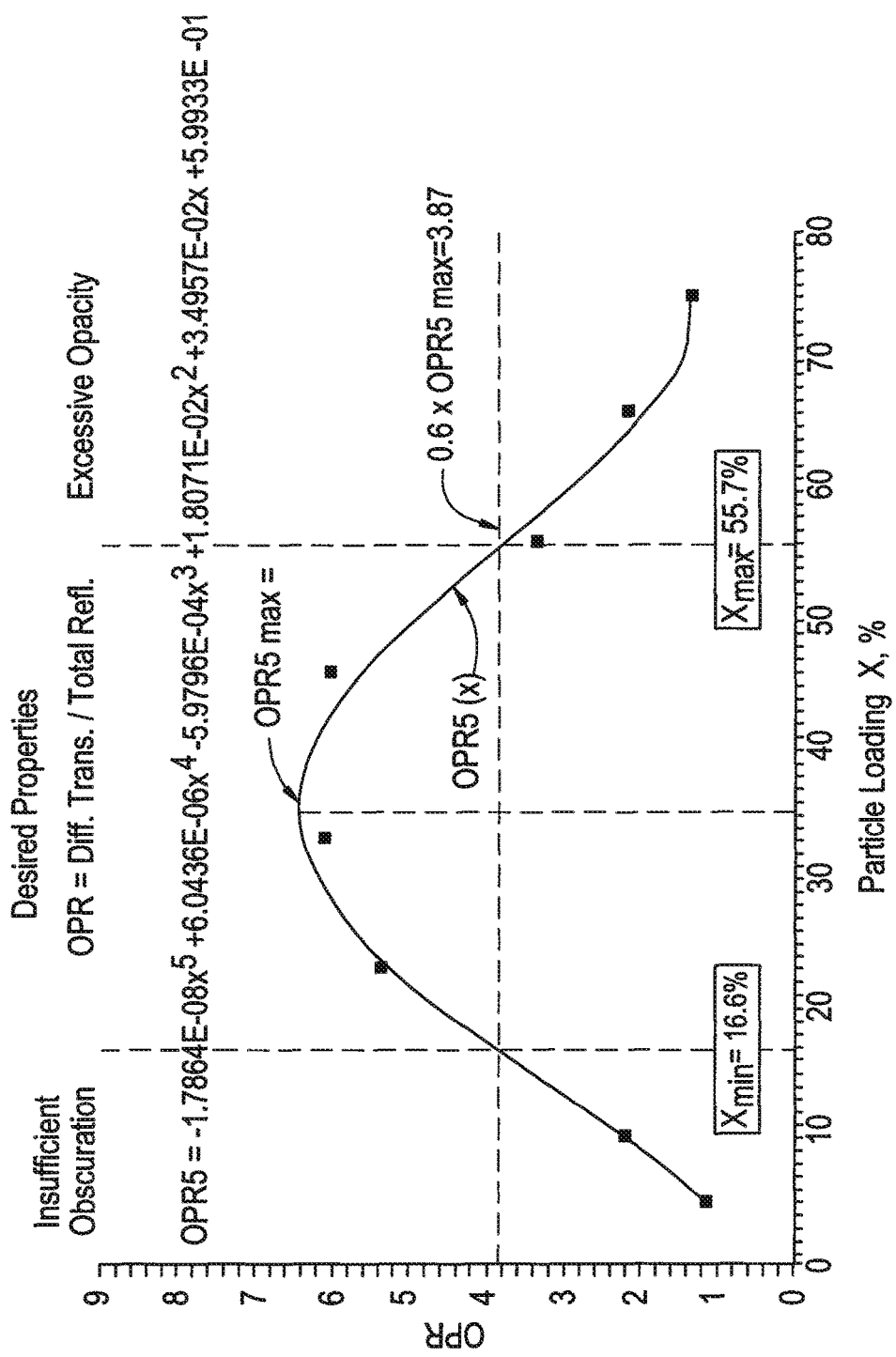

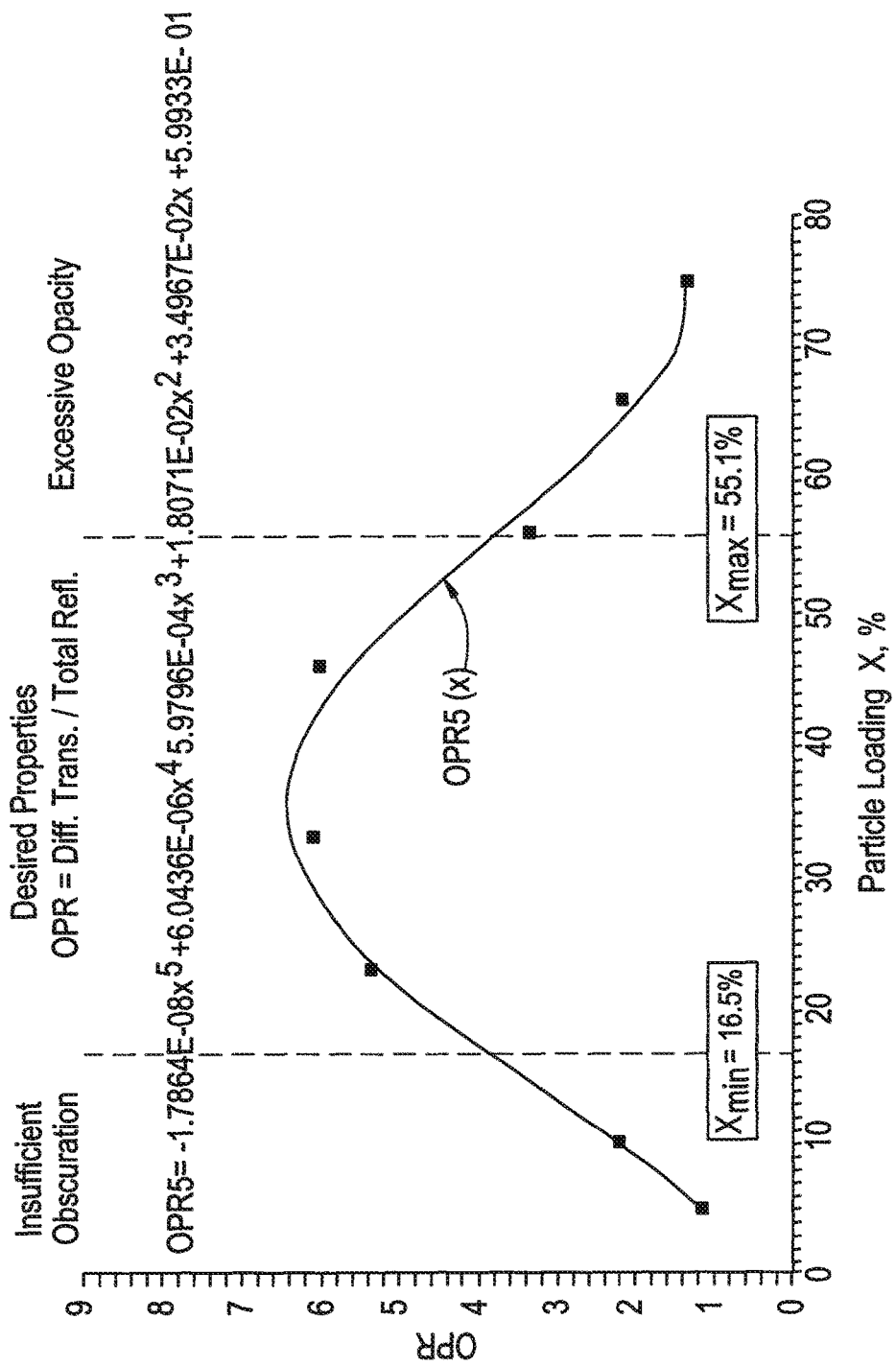

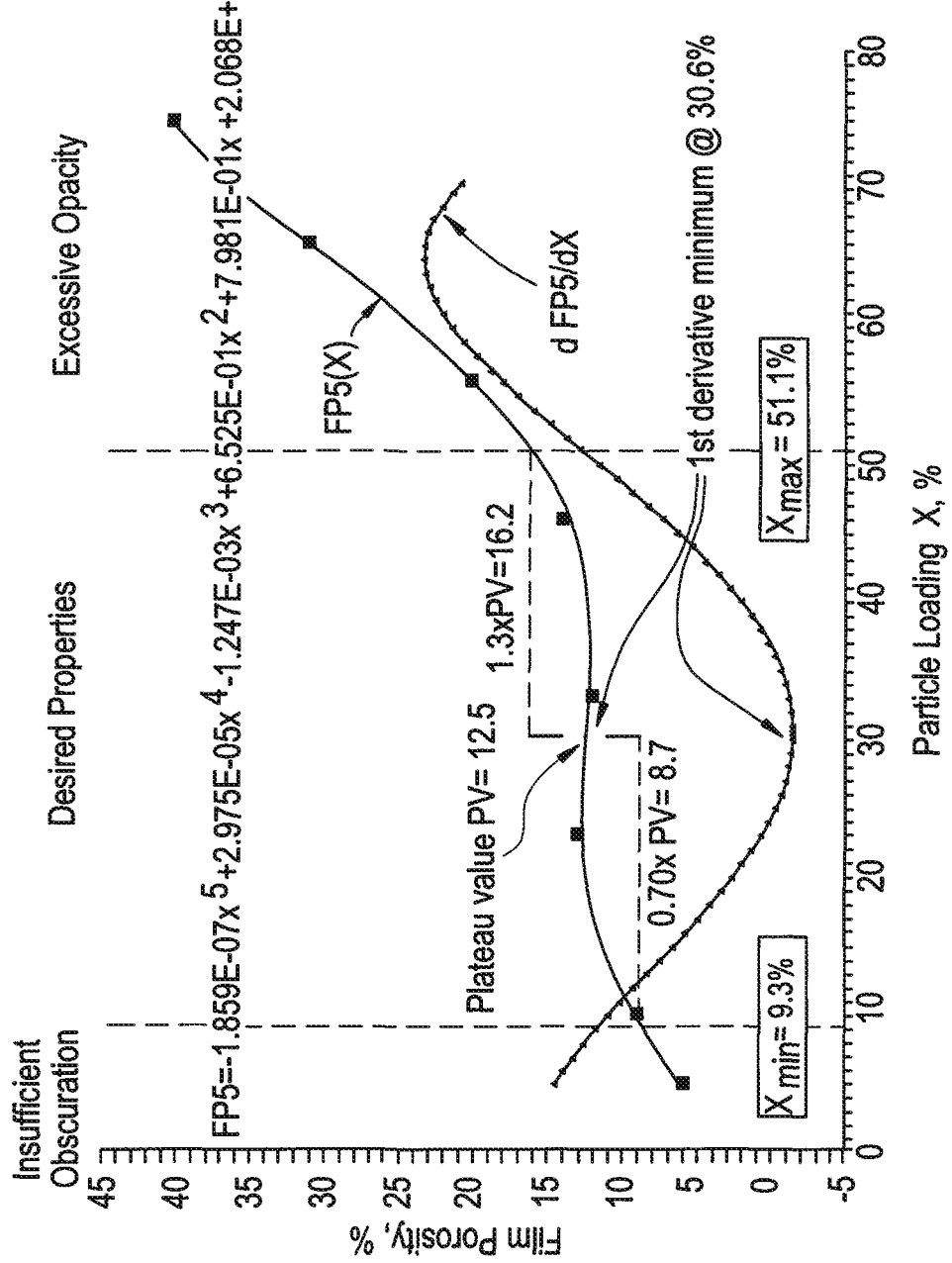

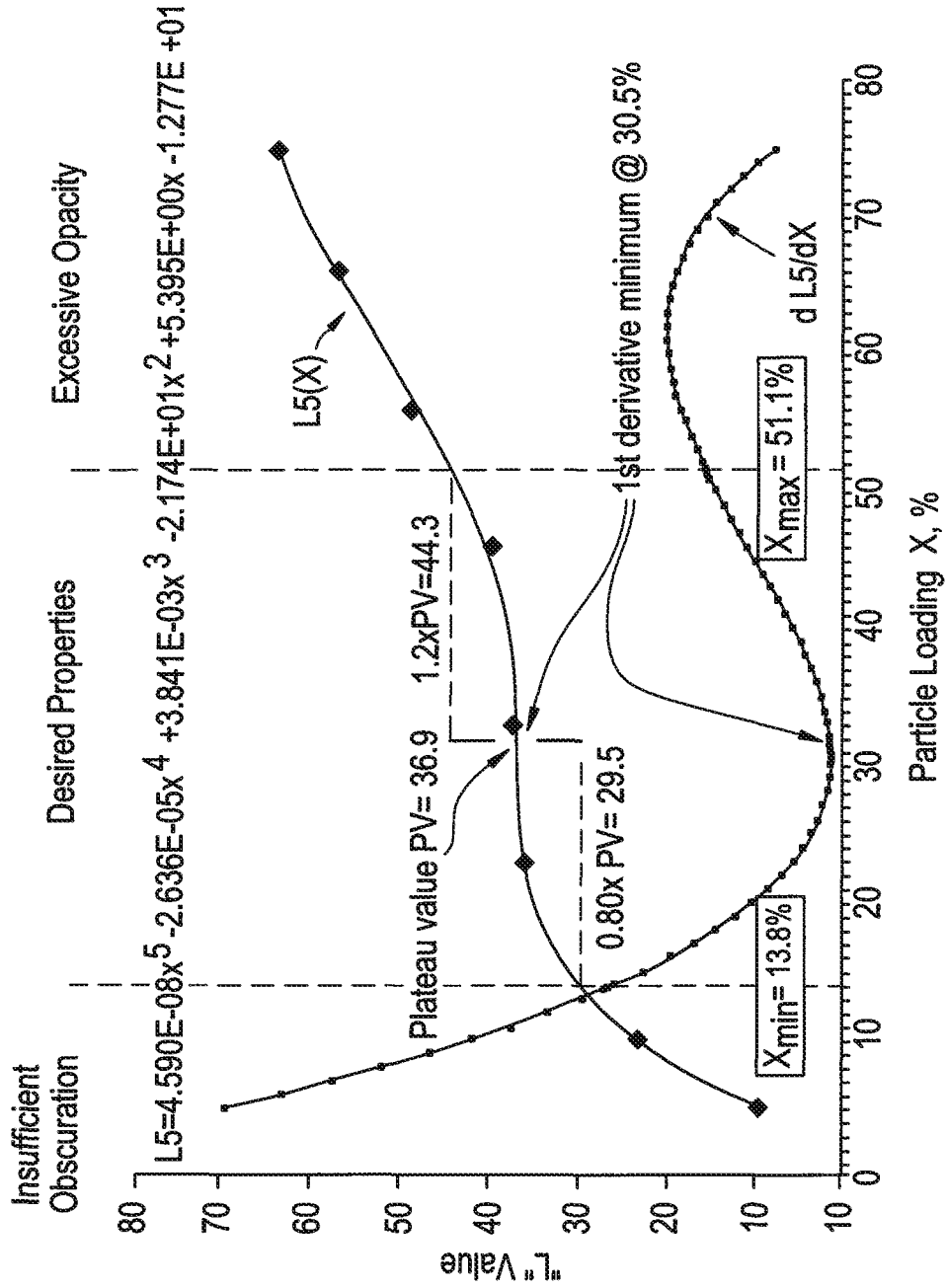

COMPOSITIONS FOR FORMING FILMS HAVING A DESIRED DEGREE OF OBSCURATION AND METHODS OF MAKING AND USING THE SAME

FIELD OF THE INVENTION

The present invention is directed to compositions suitable for use as cosmetic care products (e.g., skin creams). The present invention is further directed to methods of making and using compositions suitable for use as cosmetic care products.

BACKGROUND OF THE INVENTION

Cosmetic creams having the ability to hide wrinkles and other skin imperfections are widely used. Some creams accomplish this task by physical filling of the skin depression, giving the appearance of smooth skin. Another way to hide wrinkles and other skin imperfections is to create a film on the skin surface, which is capable of obscuring the imperfection via light diffusion. According to this method, particles present in the film scatter light producing a diffuse appearance of the underlying skin. Due to this diffuse appearance, the perception of smooth skin is created, and the unwanted skin imperfections are being obscured.

The use of light diffusing pigments for cosmetic applications has been described in *Quantification of the Soft Focus Effect, Cosmetics & Toiletries*, (Ralf Emmert), vol. 111, pp. 57-61 (1996) (hereinafter, "the Emmert article"). In the Emmert article, the use of silica in light diffusing cosmetics is discouraged due to the similarity of the refractive index of silica (RI=1.46) with that of cosmetic oils (RI=1.45-1.60). Consistent with the Emmert article was the conventional thinking that large differences in refractive index between vehicle and particle were necessary to produce a desired optical effect (i.e., maximum light scattering).

In addition, conventional thinking regarding the use of light diffusing pigments has been to load a composition with light diffusing pigments so as to maximize intra-film light scattering. FIG. 1 illustrates this principle. As shown in FIG. 1, exemplary film 10 comprises a vehicle matrix 11 with light diffusing pigments/particles 12 dispersed therein. When light 13 enters film 10 through upper surface 14, light diffusing pigments/particles scatter light 13 as shown by arrows 15. Given the surface smoothness of upper surface 14 very little light scattering takes place at upper surface 14 relative to an amount of intra-film light scattering that takes place within exemplary film 10.

Efforts continue to develop new approaches for hiding wrinkles and other skin imperfections. Efforts continue to develop obscuring compositions that are easily formulated so as to produce films and coatings that possess desired obscuration properties that are independent of film or coating thickness.

SUMMARY OF THE INVENTION

The present invention relates to the discovery of compositions suitable for use as a cosmetic care product that has the ability to hide wrinkles and other skin imperfections. The compositions may be utilized in a variety of applications, but are particularly useful as a cosmetic care product (i.e., a composition applied onto cutaneous and keratinous substrates) capable of hiding wrinkles and other imperfections.

The disclosed compositions comprise particulate material (e.g., metal oxide particles, polymeric particles, etc.) within a fluid phase that comprises at least one non-volatile component and at least one volatile component. When applied onto a substrate (e.g., cutaneous or keratinous), the disclosed compositions desirably form a continuous, transparent film that is capable of obscuring wrinkles and other imperfections in the substrate while allowing the natural tone of the substrate (e.g., a natural skin tone) to be visible through the film. Further, by having a rough outermost surface, the continuous, transparent film enables light scattering at the film surfaces, and does not rely on light scattering within the film. In another embodiment the coating is transparent such that the substrate is visible, while still providing desirable obscuration effects.

It has been discovered that the use of a coating composition comprising particulate material and a fluid phase comprising a non-volatile component and a volatile component; wherein the coating composition, after being dried on the substrate to form a coating, includes a percent particulate material, based on the percent by weight of the non-volatile component and particulate material, such that the coating possesses an optical performance ratio ranging from within 30% of the maximum optical performance ratio of a curve fit to optical performance ratio measurements of the coating at different particulate material concentrations. This exemplary embodiment produces compositions that possess superior obscuration properties, as well as a desired degree of outermost surface roughness and transparency when applied as a film onto a substrate (e.g., skin).

It has further been discovered that the use of a coating composition comprising particulate material and a fluid phase comprising a non-volatile component and a volatile component; wherein the coating composition, after being dried on the substrate to form a coating, includes percent particulate material such that the coating possesses an optical performance ratio of at least about 4.0. This exemplary embodiment produces compositions that possess superior obscuration properties, as well as a desired degree of outermost surface roughness and transparency when applied as a film onto a substrate (e.g., skin).

It has even further been discovered that the use of a coating composition comprising particulate material and a fluid phase comprising a non-volatile component and a volatile component; wherein the coating composition, after being dried on the substrate to form a coating, includes a percent by weight of particulate material, based on the percent by weight of the non-volatile component and particulate material, such that the coating possesses a porosity ranging from 30% less or greater than the porosity determined by taking the minimum of a first derivative of a curve fit to porosity measurements of the coating at different particulate material concentrations. This exemplary embodiment produces compositions that possess superior obscuration properties, as well as a desired degree of outermost surface roughness and transparency when applied as a film onto a substrate (e.g., skin).

It has even further been discovered that the use of a coating composition comprising particulate material and a fluid phase comprising a non-volatile component and a volatile component; wherein the coating composition, after being dried on the substrate to form a coating, includes a percent by weight particulate material, based on the percent by weight of the non-volatile component and particulate material, such that the coating possesses an L value ranging from 20% less or greater than the L value determined by taking the minimum of a first derivative of a curve fit to L value measurements of the coating at different particulate material concentrations. This exemplary embodiment produces compositions that possess superior obscuration properties, as well as a desired degree of outermost surface roughness and transparency when applied as a film onto a substrate (e.g., skin).

Although a variety of particulate material may be used to form the obscuring compositions and films of the present invention, it has been discovered that, in some embodiments, the use of particles that have a refractive index similar to that of the non-volatile component present in the composition/film results in enhanced obscuration properties in the resulting film. In these embodiments, the particles within the film are substantially ineffective as light scatterers; however, when incorporated into a film with an appropriate amount of the non-volatile(s), the resulting film has desired obscuration properties due to scattering of transmitted light as the result of the uneven (i.e., rough) outermost surface of the film. By restricting light scattering to the outermost surface of the film, the obscuring properties of the film are independent of film thickness. Consequently, a film applied over cutaneous or keratinous substrates desirably provides a very uniform appearance, both in obscuration and reflectance, to the substrate even if the film thickness is not particularly uniform.

Another benefit resulting from light scattering at the outermost surface of a film versus light scattering within the film is the fact that the obscuration property of a rough film is less dependent on the particle concentration in the film composition when compared to films in which infra-film light scattering is the dominant mechanism. Consequently, the present invention allows a composition/film formulator greater freedom (1) to vary the amount of particulate material within a given composition, as well as (2) to incorporate other ingredients (e.g., emollients, fragrances, soluble polymers, etc.) into the given composition.

One exemplary embodiment relates to the use of a coating comprising particulate material and a fluid phase comprising a non-volatile component and a volatile component; wherein the coating includes a percent particulate material, based on the percent by weight of the non-volatile component and particulate material, such that the coating possesses an optical performance ratio ranging from within 30% of the maximum optical performance ratio of a curve fit to optical performance ratio measurements of the coating at different particulate material concentrations. This exemplary embodiment produces coatings that possess superior obscuration properties, as well as a desired degree of outermost surface roughness and transparency on a substrate (e.g., skin). The present invention is further directed to methods of using the compositions of the present invention. The obscuring coating compositions may be formed on a variety of substrates, such as animate and inanimate substrates including, but not limited to, skin.

Another exemplary embodiment relates to the use of a coating comprising particulate material and a fluid phase comprising a non-volatile component and a volatile component; wherein the coating composition includes percent particulate material such that the coating possesses an optical performance ratio of at least about 4.0. This exemplary embodiment produces coatings that possess superior obscuration properties, as well as a desired degree of outermost surface roughness and transparency on a substrate (e.g., skin).

A further exemplary embodiment of the present invention relates to a coating comprising particulate material and a fluid phase including a non-volatile component and a volatile component, wherein the coating includes a percent by weight of particulate material, based on the percent by weight of the non-volatile component and particulate material, such that the coating possesses a porosity ranging from 30% less or greater than the porosity determined by taking the minimum of a first derivative of a curve fit to porosity measurements of the coating at different particulate material concentrations. Compositions of the present invention may further comprise one or more additional components including, but not limited to, deionized water, a humectant, an emollient, a fragrance, soluble polymers, solidified polymers, or any combination thereof.

Another exemplary embodiment of the present invention relates to a coating comprising particulate material and a fluid phase including a non-volatile component and a volatile component, wherein the coating includes a percent by weight particulate material, based on the percent by weight of the non-volatile component and particulate material, such that the coating possesses an L value ranging from 20% less or greater than the L value determined by taking the minimum of a first derivative of a curve fit to L value measurements of the coating at different particulate material concentrations.

The present invention is also directed to methods of making compositions capable of obscuring surface imperfections. In one exemplary embodiment, the method of making a coating composition comprises forming a mixture including particulate material and a fluid phase including a non-volatile component, and a volatile component; wherein the coating composition, after being dried on a substrate to form a coating, includes a percent particulate material, based on the percent by weight of the non-volatile component and particulate material, such that the coating possesses an optical performance ratio ranging from within 30% of the maximum optical performance ratio of a curve fit to optical performance ratio measurements of the coating at different particulate material concentrations. This exemplary embodiment produces coatings that possess superior obscuration properties, as well as a desired degree of outermost surface roughness and transparency on a substrate (e.g., skin).

In another exemplary embodiment, the method of making a coating composition comprises forming a mixture including particulate material and a fluid phase including a non-volatile component, and a volatile component; wherein the coating composition includes percent particulate material such that the coating possesses an optical performance ratio of at least about 4.0. This exemplary embodiment produces coatings that possess superior obscuration properties, as well as a desired degree of outermost surface roughness and transparency on a substrate (e.g., skin).

In another exemplary embodiment, the method of making a coating composition comprises forming a mixture including particulate material and a fluid phase including a non-volatile component, and a volatile component; wherein the coating composition, after being dried on the substrate to form a coating, includes a percent by weight of particulate material, based on the percent by weight of the non-volatile component and particulate material, such that the coating possesses a porosity ranging from 30% less or greater than the porosity determined by taking the minimum of a first derivative of a curve fit to porosity measurements of the coating at different particulate material concentrations. The method of making a composition may further comprise incorporating one or more additional components into the mixture, wherein the one or more additional components include, but are not limited to, deionized water, a humectant, an emollient, a fragrance, or any combination thereof.

In a further exemplary embodiment, the method of making a coating composition comprises forming a mixture including particulate material and a fluid phase including a non-volatile component, and a volatile component; wherein the coating composition, after being dried on the substrate to form a coating, includes a percent by weight particulate material, based on the percent by weight of the non-volatile component and particulate material, such that the coating possesses an L value ranging from 20% less or greater than the L value determined by taking the minimum of a first derivative of a curve fit to L value measurements of the coating at different particulate material concentrations. The method of making a composition may further comprise incorporating one or more additional components into the mixture, wherein the one or more additional components include, but are not limited to, deionized water, a humectant, an emollient, a fragrance, or any combination thereof.

The present invention is further directed to multi-layer articles comprising a substrate and the composition of the present invention on an outer surface of the substrate. In one exemplary embodiment, the multi-layer article comprises skin having an outer skin surface; and the herein disclosed obscuring composition on the outer skin surface.

These and other features and advantages of the present invention will become apparent after a review of the following detailed description of the disclosed embodiments and the appended claims.

BRIEF DESCRIPTION OF THE FIGURES

FIG. 4 depicts a graph of optical performance ratio measurements for the exemplary particle or particulate material loaded film of the present invention;

FIG. 5 depicts a graph of optical performance ratio measurements for the exemplary particle or particulate material loaded film of the present invention;

FIG. 6 depicts a graph of porosity measurements for the exemplary particle of particulate material loaded film of the present invention; and FIG. 7 depicts a graph of L value measurements for the exemplary particle or particulate material loaded film of the present invention.

DETAILED DESCRIPTION OF THE INVENTION

Figure 1:
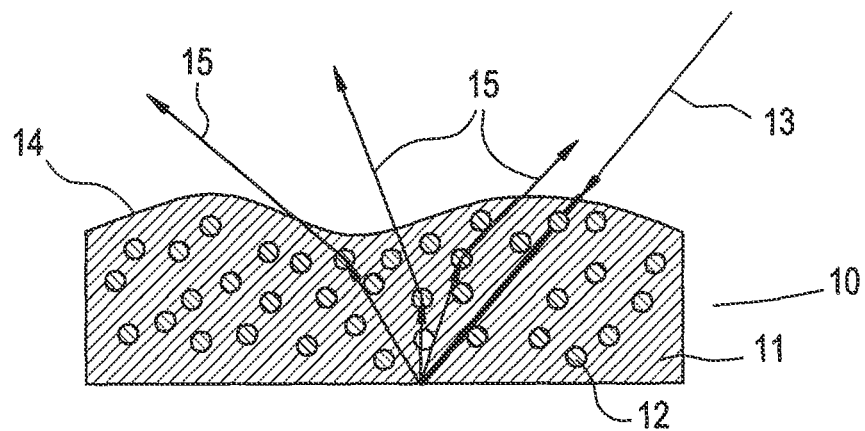
FIG. 1 depicts an exemplary conventional light diffusing pigment/particle loaded film so as to maximize intra-film light scattering.

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

It must be noted that as used herein and in the appended claims, the singular forms "a", "and", and "the" include plural referents unless the context clearly dictates otherwise. Thus, for example, reference to "an oxide" includes a plurality of such oxides and reference to "oxide" includes reference to one or more oxides and equivalents thereof known to those skilled in the art, and so forth.

"About" modifying, for example, the quantity of an ingredient in a composition, concentrations, volumes, process temperatures, process times, recoveries or yields, flow rates, and like values, and ranges thereof, employed in describing the embodiments of the disclosure, refers to variation in the numerical quantity that may occur, for example, through typical measuring and handling procedures; through inadvertent error in these procedures; through differences in the ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

As used herein, the term "film porosity" means the internal porosity of films comprising particulate material and non-volatile component formed on glass and measured by ASTM D6583-04.

As used herein, the term "fluid" means a gas, liquid, and supercritical fluid, including fluids that are volatile and non-volatile, and are natural and synthetic. Examples include, but are not limited to, oils, solvents, water, polymers, waxes, glycerin, other liquids, and mixtures thereof.

As used herein, the term "L value" means a measure of the opacity of films or coatings as defined herein. The L values of transparent films will be lower than those of opaque films.

As used herein, "metal oxides" is defined as binary oxygen compounds where the metal is the cation and the oxide is the anion. The metals may also include metalloids. Metals include those elements on the left of the diagonal line drawn from boron to polonium on the periodic table. Metalloids or semi-metals include those elements that are on the right of this line. Examples of metal oxides include silica, alumina, titania, zirconia, etc., and mixtures thereof.

As used herein, the term "optical performance ratio" means the ratio of diffuse transmittance to total reflection and is a measure of the obscuration and transparency of a material or coating.

As used herein, "organic" materials include those compounds or materials that include carbon content, which may be natural or synthetic. These materials may be natural and/or synthetic polymers that may be homopolymers or copolymers and include, but are not limited to, biopolymers, fluoropolymers, polyterpenes, phenolic resins, polyanhydrides, polyesters, polyolefins, rubbers, silicones, superabsorbent polymers, vinyl polymers, and combinations thereof. Examples of organic materials include, but are not limited to, polypropylenes, polyethylenes, polyamides, polytetrafluoroethylenes, polymethylmethacrylates, silicones, etc., and mixtures thereof.

As used herein, the term "obscuration" refers to the hiding of uneven or imperfect substrate surface morphology using films or coatings and is measured according to the method set forth herein.

As used herein, the term "particulate material" refers to porous or nonporous particles formed via any known process including, but not limited to, a solution polymerization process such as for forming colloidal particles, a continuous flame hydrolysis technique such as for forming fused particles, a gel technique such as for forming gelled particles, and a precipitation technique such as for forming precipitated particles. The particles may be composed of organic and/or inorganic materials and combinations thereof. In one exemplary embodiment the particles are composed of inorganic materials such as metal oxides, sulfides, hydroxides, carbonates, silicates, phosphates, etc, but are preferably metal oxides. The particles may be a variety of different symmetrical, asymmetrical or irregular shapes, including chain, rod or lath shape. The particles may have different structures including amorphous or crystalline, etc. The particles may include mixtures of particles comprising different compositions, sizes, shapes or physical structures, or that may be the same except for different surface treatments. Preferably, the metal oxide particles are amorphous.

As used herein the term "porous particles" means particles having significant internal porosity as measured by nitrogen porisimetry, i.e., a porosity of more than about 0.05 cc/g, and the term "non-porous" means particles having little or no internal porosity, i.e., an internal porosity of less than about 0.05 cc/g. Examples of porous particles include, silica gel, precipitated silica, fumed silica, boehmite alumina, etc., and examples of non-porous particles include colloidal silica, alumina, titania, etc.

As used herein, the term "light scattering" or other electromagnetic radiation is the deflection of rays in random directions by irregularities in the propagation medium, or in a surface or interface between two media. Scattering from a surface or interface can also be called diffuse reflection.

As used herein, the term "substantially" means within a reasonable amount, but includes amounts which vary from about 0% to about 50% of the absolute value, from about 0% to about 40%, from about 0% to about 30%, from about 0% to about 20% or from about 0% to about 10%.

The disclosed compositions comprise particulate material (e.g., silica particles) within a fluid phase that comprises at least one non-volatile component and at least one volatile component. When applied onto a substrate (e.g., cutaneous or keratinous), the disclosed compositions desirably form a continuous, transparent film that is capable of obscuring wrinkles and other imperfections in the substrate while allowing the natural tone of the substrate (e.g., a natural skin tone) to be visible through the film. Further, by having a rough outermost surface, the continuous, transparent film enables light scattering at the film surfaces, and does not rely on light scattering within the film.

The present invention is directed to compositions comprising (i) particulate material, and (ii) a fluid phase comprising a non-volatile component and a volatile component. The present invention is further directed to methods of making compositions comprising (i) particulate material, and (ii) a fluid phase comprising a non-volatile component and a volatile component. The present invention is even further directed to methods of forming a coating or film on a substrate, wherein the coating or film comprises (i) particulate material, and (ii) a fluid phase comprising a non-volatile component and a volatile component. The present invention is even further directed to coatings or film, coated substrates, and multi-layer articles comprising the disclosed composition on a substrate such as skin.

The compositions of the present invention provide one or more benefits and/or technical advantages that were not previously addressed in the art of compositions and coatings formed therefrom. For example, the disclosed compositions and resulting coatings utilize (i) particulate material, and (ii) a fluid phase comprising a non-volatile component and a volatile component in amounts that enable the formation of coatings and films having (1) a desired degree of film porosity, (2) a desired degree of transparency, and (3) a desired degree of obscuration properties.

It has been discovered that the use of a coating composition comprising particulate material and a fluid phase comprising a non-volatile component and a volatile component; wherein the coating composition, after being dried on the substrate to form a coating, includes a percent particulate material, based on the percent by weight of the non-volatile component and particulate material, such that the coating possesses an optical performance ratio ranging from within 30% (or 25%, 20%, 15%, 10%, or even 5%) of the maximum optical performance ratio of a curve fit to optical performance ratio measurements of the coating at different particulate material concentrations. This exemplary embodiment produces compositions that possess superior obscuration properties, as well as a desired degree of outermost surface roughness and transparency when applied as a film onto a substrate (e.g., skin).

It has further been discovered that the use of a coating composition comprising particulate material and a fluid phase comprising a non-volatile component and a volatile component; wherein the coating composition, after being dried on the substrate to form a coating, includes percent particulate material such that the coating possesses an optical performance ratio of at least about 4.0 (or 4.5, 5.0, 5.5 or even 6.0). This exemplary embodiment produces compositions that possess superior obscuration properties, as well as a desired degree of outermost surface roughness and transparency when applied as a film onto a substrate (e.g., skin).

It has further been discovered that the use of a coating composition comprising particulate material and a fluid phase comprising a non-volatile component and a volatile component; wherein the coating composition, after being dried on the substrate to form a coating, includes a percent by weight of particulate material, based on the percent by weight of the non-volatile component and particulate material, such that the coating possesses a porosity ranging from 30% (or 25%, 20%, 15%, 10%, or even 5%) less or greater than the porosity determined by taking the minimum of a first derivative of a curve fit to porosity measurements of the coating at different particulate material concentrations. This exemplary embodiment produces compositions that possess superior obscuration properties, as well as a desired degree of outermost surface roughness and transparency when applied as a film onto a substrate (e.g., skin).

It has even further been discovered that the use of a coating composition comprising particulate material and a fluid phase comprising a non-volatile component and a volatile component; wherein the coating composition, after being dried on the substrate to form a coating, includes a percent by weight particulate material, based on the percent by weight of the non-volatile component and particulate material, such that the coating possesses an L value ranging from 20% (or 15%, 10%, or even 5%) less or greater than the L value determined by taking the minimum of a first derivative of a curve fit to L value measurements of the coating at different particulate material concentrations. This exemplary embodiment produces compositions that possess superior obscuration properties, as well as a desired degree of outermost surface roughness and transparency when applied as a film onto a substrate (e.g., skin).

A description of exemplary compositions and composition components is provided below.

I. Compositions

The compositions of the present invention may comprise a number of individual components. A description of individual components and combinations of individual components is provided below. Further, the compositions of the present invention may be presented in various forms. A description of types of compositions is also provided below.

A. Composition Components

The compositions of the present invention may comprise one or more of the following components.

1. Particulate Material

The compositions of the present invention comprise particulate material having inter and/or intra particle porosity value of greater than zero. Suitable particulate materials having inter and/or intra particle porosity value of greater than zero include, but are not limited to, alumina, boron nitride, nylon, silica, silica/titania composites, and any combination thereof. For example, the particulate material may be porous or non-porous and may be in the form of a powder or slurry including aqueous and non-aqueous fluids.

Suitable particulate materials for use in the present invention have inter and/or intra particle porosity values greater than zero that depend on, for example, the particle composition, the degree of particle porosity and particle agglomeration. For example, if the particles possess no significant porosity, such as metal oxide colloidal particles, then the particulate material may possess measurable inter particle porosity in order to impart desirable film porosity. In embodiments where porous particles are utilized, the porosity in the film is generated from inter and intra particle porosity and may vary depending upon (1) the internal particle porosity, and (2) the tendency for the particles to form agglomerates.

In one embodiment, the metal oxide particulate comprises porous materials, such as precipitated metal oxide (e.g., silica, alumina, titania, etc.), metal oxide gel, or fumed metal oxide. As it is well known in the art, the formation of precipitated silica occurs in a reaction between waterglass and an acid via first forming a seed of primary particles which can be grown to larger particles, followed by an aggregation and then by an agglomeration of these aggregates. Depending on the reaction conditions, the agglomerates can be grown even more together by a so called reinforcement. At a certain agglomerate size and concentration, the hydrous silica begins to settle from the reaction slurry as a precipitate. To isolate the hydrous silica from the slurry and to remove the reaction electrolyte from the crude silica, the precipitate is filtered from the slurry and washed. The resulting filtercake then is dried using drying equipment as known in the art. Depending on the method and extend of drying, a stiffening of the silica structure will occur during the drying step in which irreversible Si—O—Si-links are formed from initial silanol groups. Processes for making precipitated metal oxides include those set forth in U.S. Pat. Nos. 7,037,475B1; 5,030,286 and 4,157,920, the entire subject matter of which is incorporated herein by reference. In a further embodiment of the present invention, the colloidal metal oxide particles stem from the primary particles, grown particles, aggregated particles, agglomerated particles or the filtercake of a general metal oxide precipitation process as described above.

Methods of preparing metal oxide gels are well known in the art and include those set forth in U.S. Pat. No. 6,380,265, the entire subject matter of which is incorporated herein by reference. For example, a silica gel is prepared by mixing an aqueous solution of an alkali metal silicate (e.g., sodium silicate) with a strong acid such as nitric or sulfuric acid, the mixing being done under suitable conditions of agitation to form a clear silica sol which sets into a hydrogel, i.e., macrogel, in less than about one-half hour. The resulting gel is then washed. The concentration of metal oxide, i.e., $SiO_2$, formed in the hydrogel is usually in the range of about 10 and about 50 weight percent, with the pH of that gel being from about 1 to about 9, preferably 1 to about 4. A wide range of mixing temperatures can be employed, this range being typically from about 20 to about 50° C. The newly formed hydrogels are washed simply by immersion in a continuously moving stream of water which leaches out the undesirable salts, leaving about 99.5 weight percent or more pure metal oxide behind. The pH, temperature, and duration of the wash water will influence the physical properties of the silica, such as surface area (SA) and pore volume (PV). Silica gel washed at 65-90° C. at pH's of 8-9 for 15-36 hours will usually have SA's of 250-400 and form aerogels with PV's of 1.4 to 1.7 cc/gm. Silica gel washed at pH's of 3-5 at 50-65° C. for 15-25 hours will have SA's of 700-850 and form aerogels with PV's of 0.6-1.3. These measurements are generated by $N_2$ porosity analysis. Methods for preparing metal oxide gels such as alumina and mixed metal oxide gels such as silica/alumina cogels are also well known in the art. Methods for preparing such gels are disclosed in U.S. Pat. No. 4,226,743, the contents of which are incorporated by reference. In general, alumina gels are prepared by mixing alkali metal aluminates and aluminum sulfate. Cogels are prepared by cogelling two metal oxides so that the gels are composited together. For example, silica alumina cogels can be prepared by gelling an alkali metal silicate with an acid or acid salt, and then adding alkali metal aluminate, aging the mixture and subsequently adding aluminum sulfate. The gel is then washed using conventional techniques.

In embodiments where the particulate material comprises porous particles, they generally possess a pore volume that makes the particles desirable formulation components and to provide desirable porosity to the resulting film. Typically, the porous particles have a pore volume as measured by nitrogen porosimetry of at least about 0.20 cc/g, and more typically, 0.30 cc/g. In one exemplary embodiment of the present invention, the porous particles have a pore volume as measured by nitrogen porosimetry of at least about 0.30 cc/g. Desirably, the porous particles have a pore volume as measured by nitrogen porosimetry of from about 0.30 to about 0.85 cc/g.

Porous particulate material of the present invention may also have a surface area as measured by the BET method (i.e., the Brunauer Emmet Teller method) of at least about 110 $m^2$/g. In one exemplary embodiment of the present invention, the porous particles have a BET surface area of from about 150 $m^2$/g to about 220 $m^2$/g. In a further exemplary embodiment of the present invention, the porous particles have a BET surface area of about 172 $m^2$/g.

Pore volume and surface area may be measured using, for example, an Autosorb 6-B unit commercially available from Quantachrome Instruments (Boynton Beach, Fla.). Typically, the pore volume and surface area of porous particulate material is measured after drying at about 150° C., and degassing for about 3 hours at 150° C. under vacuum (e.g., 50 mlllitorr).

The particulate materials typically have an average particle size ranging from about 0.1 to about 35 microns (μm). As used herein, the term "average particle size" refers to the average of the largest dimension of each particle within a set of particles. In some exemplary embodiments, the particulate materials have an average particle size ranging from about 1 to about 20 μm. In more desired embodiments, the particulate materials have an average particle size ranging from about 2 to about 10 μm (e.g., equal to or less than about 10, 9, 8, 7, 6, 5, 4, 3, 2, 1 microns and any size below one micron including 900, 800, 700, 600, 500, 400, 300, 200, or 100 nanometers, and even less than about 100 nanometers).

The particulate materials are typically present in the compositions of the present invention in an amount greater than 0 weight percent (wt %) and up to about 80 wt % based on a total weight of the composition. In some exemplary embodiments, the compositions comprise one or more particulate materials in an amount ranging from about 1 wt % to about 50 wt %, more typically, from about 1 wt % to about 20 wt %, and even more typically, from about 1 wt % to about 10 wt %, based on a total weight of the composition. For some exemplary embodiments of cream formulations, the amount of particulate material typically present in the formulation may be greater than 0 wt % up to about 20 wt %, more typically, from about 1 wt % to about 10 wt %, and even more typically, from about 2 wt % to about 8 wt %, based on the total weight of composition. For some exemplary embodiments of powder formulations, the amount of particulate material present in the formulations may be from about 1 wt % to about 80 wt %, from about 3 wt % to about 70 wt %, from about 5 wt % to about 60, or even from about 10 wt % to about 55 wt %, based on the total weight of the composition.

In some exemplary embodiments, it may be beneficial to choose particulate material(s) having a refractive index (RI) that either matches or is relatively close to the refractive index of one or more component fluids used in the fluid phase (discussed below). Typically, the particulate material(s) have a refractive index (RI) ranging from about 1.2 to about 1.8. In some exemplary embodiments, the particulate material comprises silica particles having a refractive index of about 1.4 to about 1.6.

In an exemplary embodiment, the particulate materials may be surface treated to change the surface properties of the materials. For example, the surface of the particulate materials may be treated to render them hydrophobic, such as by treatment with various organic materials (e.g., silanes, siloxanes, etc.). Since the surfaces of certain metal oxides are very hydrophilic (e.g., silica), the particulates tend to aggregate or agglomerate into larger particulates. If the surface of the metal oxide particulates is treated with hydrophobic material, the particulates do not aggregate, thereby remaining discrete and stable particles. Such hydrophobic materials include a variety of organic compounds, such as silanes, esters, alcohols, etc., and examples for rendering hydrophilic metal oxides hydrophobic may be found in U.S. Pat. Nos. 2,786,042 and 2,801,185, the entire subject matter of which is incorporated herein by reference. U.S. Pat. Nos. 6,344,240; 6,197,384; 3,924,032; and 3,657,680; and EP 0658523, describe various particulate surface treatments that may be utilized in this embodiment of the present invention, the entire subject matter of which is incorporated herein by reference.

In another exemplary embodiment, the particulate material may include a combination of various types of particulate material, such as particles of different size, shape, porosity, composition, refractive index, etc.

2. Fluid Phase Materials

The compositions of the present invention also comprise a fluid phase comprising a non-volatile component and a volatile component. The fluid phase may comprise a single fluid product having both a non-volatile component and a volatile component that are miscible with each other, or two or more fluid products that, in combination, contribute to the non-volatile component and the volatile component (i.e., separate phases).

The fluid phase is typically present in the compositions of the present invention in an amount greater than 0 wt % and up to about 60.0 wt % based on a total weight of the composition. In some exemplary embodiments, the compositions comprise a fluid phase in an amount ranging from about 10.0 wt % to about 98.0 wt %, more typically, from about 25.0 wt % to about 80.0 wt %, and even more typically, from about 35.0 wt % to about 65.0 wt %, based on a total weight of the composition.

Typically, the non-volatile component and the volatile component may be present in any amount relative to one another as long as a desired value for R results from the combination. In some exemplary embodiments, the fluid phase comprises from about 1.0 to about 60.0 wt % of the non-volatile component, and from about 99.0 to about 40.0 wt % of the volatile component, based on a total weight of the fluid phase. In further exemplary embodiments, the fluid phase comprises from about 1.0 to about 40.0 wt % of the non-volatile component, and from about 99.0 to about 60.0 wt % of the volatile component, based on a total weight of the fluid phase. In other exemplary embodiments, the fluid phase comprises from about 1.6 to about 16.0 wt % of the non-volatile component, and from about 98.4 to about 84.0 wt % of the volatile component, based on a total weight of the fluid phase.

In some exemplary embodiments, it may be beneficial to choose one or more fluids having a refractive index (RI) that either matches or is relatively close to the refractive index of one or more particulate material. Typically, suitable fluids have a refractive index (RI) ranging from about 1.2 to about 1.8. In some exemplary embodiments, the one or more fluids have a refractive index of about 1.4 to about 1.6.

Suitable non-volatile components include, but are not limited to, oils, such as olive oils, sunflower oils, and the like; waxes, such as polyethylene waxes, and the like; glycerin; soluble polymers; and mixtures thereof. A number of commercially available products contributing to the non-volatile components may be used in the present invention, including, but not limited to, fluids commercially available under the trade designation DOW CORNING® 1501, DOW CORNING® 5329 and DOW CORNING® 5200, all of which are commercially available from Dow Corning, Corporation (Midland, Mich.); Crodamol CP, Crodamol DIBA, Crodamol MM, Crodamol GTCC, Crodamol ICS, all of which are available from Croda Inc.; Cetiol J-600, Cetiol A, Cetiol 868, Cetiol CC, Cetiol LDO, all of which are available from Cognis Corporation.

Suitable volatile components include, but are not limited to, volatile silicones, such as DOW CORNING® 245 Fluid; water; solvents, such as ethanol; volatile fragrances; and the like; and mixtures thereof.

6. Additional Ingredients

The compositions of the present invention may further comprise one or more additional components. Suitable additional components for use in the compositions of the present invention include, but are not limited to, deionized (DI) water, humectants, surfactants, emollients, fragrances, polymers (including insoluble polymers which may form secondary particles, or soluble polymers) or any combination thereof.

Typically, the compositions of the present invention comprise deionized (DI) water. When present, the deionized (DI) water is present in an amount ranging from about 50 to about 90 wt % based on a total weight of a given composition. In some exemplary embodiments, deionized (DI) water is present in a given composition in an amount ranging from about 60 wt % to about 80 wt %, more typically, from about 70 wt % to about 76 wt %, and even more typically, from about 72 wt % to about 74 wt %, based on a total weight of the composition. However, the amount of deionized (DI) water, when present, may vary as desired.

Each additional component, other than deionized (DI) water (e.g., a humectant, an emollient, or a fragrance), may be present in an amount ranging from greater than 0 to about 30 wt % based on a total weight of a given composition B. Composition Forms The compositions of the present invention may have one or more of the following forms.

1. Suspensions or Dispersions

The compositions of the present invention are typically formulated as a suspension or dispersion having a viscous liquid matrix (e.g., the fluid phase) and particulate material suspended within the viscous liquid matrix.

One exemplary embodiment of the present invention relates to the use of a coating composition comprising particulate material and a fluid phase comprising a non-volatile component and a volatile component; wherein the coating composition, after being dried on the substrate to form a coating, includes a percent particulate material, based on the percent by weight of the non-volatile component and particulate material, such that the coating possesses an optical performance ratio ranging from within 30% (or 25%, 20%, 15%, 10%, or even 5%) of the maximum optical performance ratio of a curve fit to optical performance ratio measurements of the coating at different particulate material concentrations. This exemplary embodiment produces compositions that possess superior obscuration properties, as well as a desired degree of outermost surface roughness and transparency when applied as a film onto a substrate (e.g., skin).

Another exemplary embodiment of the present invention relates to the use of a coating composition comprising particulate material and a fluid phase comprising a non-volatile component and a volatile component; wherein the coating composition, after being dried on the substrate to form a coating, includes percent particulate material such that the coating possesses an optical performance ratio of at least about 4.0 (or 4.5, 5.0, 5.5 or 6.0). This exemplary embodiment produces compositions that possess superior obscuration properties, as well as a desired degree of outermost surface roughness and transparency when applied as a film onto a substrate (e.g., skin).

A further exemplary embodiment of the present invention relates to a coating composition comprising particulate material and a fluid phase including a non-volatile component and a volatile component, wherein the coating composition, after being dried on the substrate to form a coating, includes a percent by weight of particulate material, based on the percent by weight of the non-volatile component and particulate material, such that the coating possesses a porosity ranging from 30% (or 25%, 20%, 15%, 10%, or even 5%) less or greater than the porosity determined by taking the minimum of a first derivative of a curve fit to porosity measurements of the coating at different particulate material concentrations. This exemplary embodiment produces compositions that possess superior obscuration properties, as well as a desired degree of outermost surface roughness and transparency when applied as a film onto a substrate (e.g., skin). Compositions of the present invention may further comprise one or more additional components including, but not limited to, deionized water, a humectant, an emollient, a fragrance, soluble polymers, solidified polymers, or any combination thereof.

An even further exemplary embodiment of the present invention relates to a coating composition comprising particulate material and a fluid phase including anon-volatile component and a volatile component, wherein the coating composition, after being dried on the substrate to form a coating, includes a percent by weight particulate material, based on the percent by weight of the non-volatile component and particulate material, such that the coating possesses an L value ranging from 20% (or 15%, 10%, or even 5%) less or greater than the L value determined by taking the minimum of a first derivative of a curve fit to L value measurements of the coating at different particulate material concentrations. This exemplary embodiment produces compositions that possess superior obscuration properties, as well as a desired degree of outermost surface roughness and transparency when applied as a film onto a substrate (e.g., skin).

2. Films or Coatings

The compositions of the present invention may also be present as a film or coating on a substrate, such as skin. Typically, following application of a given composition of the present invention onto a substrate (e.g., skin) in film form, at least a portion of the volatile component evaporates from the composition, leaving a film having a construction as shown in FIG. 2.

Figure 2:
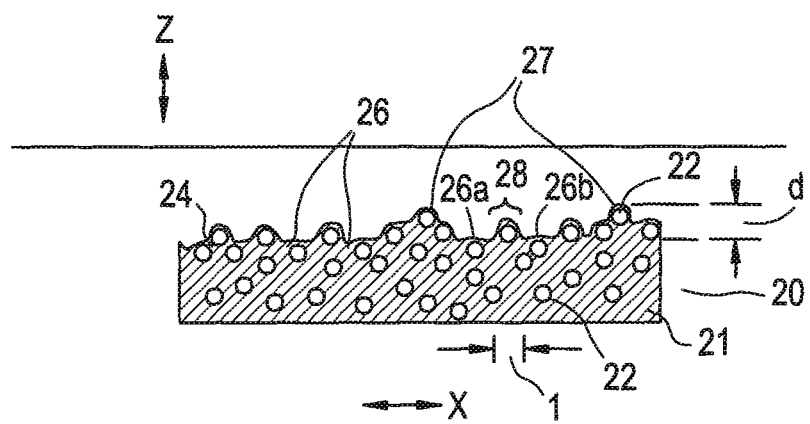
FIG. 2 depicts an exemplary particle or particulate material loaded film of the present invention.

As shown in FIG. 2, exemplary film 20 comprises a vehicle matrix 21 (e.g., the fluid phase) with particulate material 22 dispersed therein. Exemplary film 20 also has a rough upper surface 24 that results in a substantial amount of light scattering at upper surface 24. Typically, exemplary film 20 exhibits very little, if any, intra-film light scattering given the surface morphology of upper surface 24.

As shown in FIG. 2, upper surface 24 comprises one or more lower surface points 26 along the outermost rough surface (i.e., upper surface 24) and one or more upper surface points 27 along the outermost rough surface (i.e., upper surface 24), wherein one or more lower surface points 26 are separated from one or more upper surface points 27 in a z direction (i.e., a direction normal to the substrate on which exemplary film 20 is placed) by a distance, d, of at least about 0.1 µm, typically from about 0.1 to about 70 µm. Further, portions of upper surface 24 extending between two or more lower surface points 26 may exhibit an arc configuration having an arc angle of greater than about 45° (or greater than about 90°, or greater than about 135°), and as much as about 180° or greater. Such upper surface portions, such as upper surface portion 28 shown between lower surface point 26a and lower surface point 26b, exhibit an arc angle of as much as 180° or greater within a distance, l, extending in an x direction between lower surface point 26a and lower surface point 26b. Typically, distance, l, is less than about 20 µm, typically from about 20 to about 1 µm.

Figure 3A:
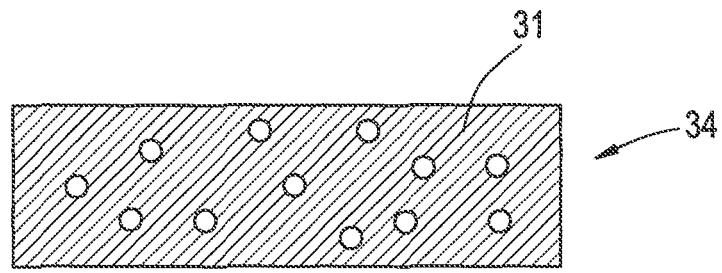
FIG. 3 (a)-(c) depict coatings or films having different particulate material loadings.
Figure 3B:
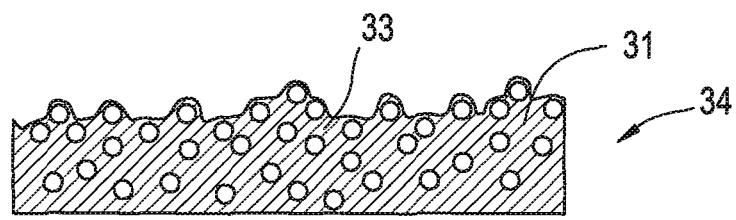
Figure 3C:
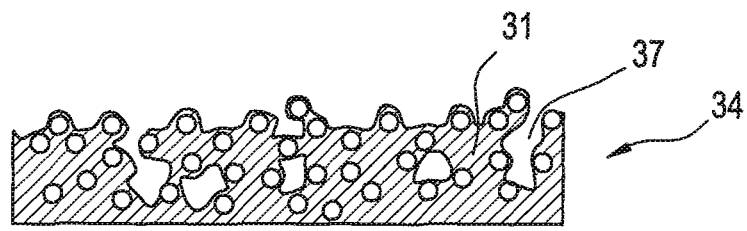

As shown in FIG. 3(a), the film 34 comprises no internal porosity (i.e., the pores and inter-particle voids are filled with fluid). After the volatile components of the fluid phase or matrix 31 evaporate, porosity of the film increases, but eventually reaches equilibrium. FIG. 3(b) depicts a roughened surface 33 as a result of higher pigment or particle loading. Once all of the volatile components have evaporated, the void portions 37 remain constant since the non-volatile components in the fluid phase remain in the film 34. FIG. 3(c) depicts a film having an internal porosity to such an extent that the film 34 becomes opaque, which significantly impairs the transparency of the film.

It has been discovered by the applicants that the obscuration effects of the coatings recited herein are impacted by a variety of components in the coating formulation, including but not limited to, the amount of particulate material utilized in the coating formulations. This in turn affects certain coating or film properties, such as porosity, L value, optical performance ratio, etc. However, the very nature of the obscuration films set forth herein impedes the ability to measure the above-mentioned properties. For example, the film forming polymers in certain coating formulations of the present invention for cosmetic applications typically do not dry or set to provide films that would allow such measurements (e.g., they remain soft, highly plastic, waxy, resinous, viscous, etc.). Accordingly, the applicants have utilized film forming polymers in the obscuration coatings of the present invention that set to provide a rigid film or coating (e.g., robust, scratch resistant, etc.), which allows for the accurate measurement of the above-mentioned properties. Such formulations are set forth in Examples 1-3.

One exemplary embodiment of the present invention relates to the use of a coating comprising particulate material and a fluid phase comprising a non-volatile component and a volatile component; wherein the coating includes a percent particulate material, based on the percent by weight of the non-volatile component and particulate material, such that the coating possesses an optical performance ratio ranging from within 30% (or 25%, 20%, 15%, 10%, or even 5%) of the maximum optical performance ratio of a curve fit to optical performance ratio measurements of the coating at different particulate material concentrations. This exemplary embodiment produces coatings that possess superior obscuration properties, as well as a desired degree of outermost surface roughness and transparency on a substrate (e.g., skin). The present invention is further directed to methods of using the compositions of the present invention. The obscuring coating compositions may be formed on a variety of substrates, such as animate and inanimate substrates including, but not limited to, skin.

For instance, as shown in FIG. 4, film optical performance ratio (OPR) values measured in Example 1 and set forth in Table 1 are plotted at different particle or pigment loadings on a graph, with the optical performance ratio value on the y axis and the particle loading wt % on the x axis. A curve is generated through the optical performance ratio value data using a best fit $5^{th}$ order polynomial (OPR5). The desired optical performance ratio value range is determined such that it is 60% greater than or equal to the maximum value of the curve (OPR5). That is, $X_{min}$ and $X_{max}$ are the X values where OPR5=0.6×OPR5. In this example, $X_{min}$ is 16.6 wt % particulate material and $X_{max}$ is 55.7 wt % based on the weight of particulate material and non-volatile component.

Another exemplary embodiment of the present invention relates to the use of a coating comprising particulate material and a fluid phase comprising a non-volatile component and a volatile component; wherein the coating composition includes percent particulate material such that the coating possesses an optical performance ratio of at least about 4.0 (or 4.5, 5.0, 5.5 or 6.0). This exemplary embodiment produces coatings that possess superior obscuration properties, as well as a desired degree of outermost surface roughness and transparency on a substrate (e.g., skin).

For example, as shown in FIG. 5, film optical performance ratio (OPR) values measured in Example 1 and set forth in Table 1 are plotted at different particle or pigment loadings on a graph, with the optical performance ratio value on the y axis and the particle loading wt % on the x axis. A curve is generated through the optical performance ratio value data using a best fit $5^{th}$ order polynomial (OPR5). The desired optical performance ratio value range is determined such that it is greater than or equal to 4.0. In this example, $X_{min}$ is 17.2 wt % particulate material and $X_{max}$ is 55.1 wt % based on the weight of particulate material and non-volatile component. Even though a $5^{th}$ order polynomial is used to curve fit the data, any polynomial, sine or cosine function, gamma function, or the like may be utilized including those set forth in the SAS User's Guide, 1979 Edition, which is incorporated herein by reference. In addition, any commercially available curve fitting software may be utilized, such as the SOLVER program available as an EXCEL add-in tool from Microsoft Corporation (Redmond, Wash.).

A further exemplary embodiment of the present invention relates to a coating comprising particulate material and a fluid phase including a non-volatile component and a volatile component, wherein the coating includes a percent by weight of particulate material, based on the percent by weight of the non-volatile component and particulate material, such that the coating possesses a porosity ranging from 30% (or 25%, 20%, 15%, 10%, or even 5%) less or greater than the porosity determined by taking the minimum of a first derivative of a curve fit to porosity measurements of the coating at different particulate material concentrations. Compositions of the present invention may further comprise one or more additional components including, but not limited to, deionized water, a humectant, an emollient, a fragrance, soluble polymers, solidified polymers, or any combination thereof.

For instance, as shown in FIG. 6, the porosity values measured in Example 1 and set forth in Table 1 are plotted at different particle or pigment loadings on a graph, with the porosity value on the y axis and the particle loading wt % on the x axis. A curve is generated through the porosity value data using a best fit $5^{th}$ order polynomial (FP5). As can be seen from FIG. 6, the curve proceeds through a plateau and the midpoint of the plateau (PV) is identified by determining the porosity value (FP) and particle loading (X) at the minimum of a first derivative of the curve (dFP5/dX). The desired porosity value range is determined such that it is 30% less and greater than PV. That is, $X_{min}$ is the X value where FP5=0.7×PV and $X_{max}$ is the X value where FP5=1.3×PV. In this example, $X_{min}$ is 9.3 wt % particulate material and $X_{max}$ is 51.1 wt % based on the weight of particulate material and non-volatile component.

An even further exemplary embodiment of the present invention relates to a coating comprising particulate material and a fluid phase including a non-volatile component and a volatile component, wherein the coating includes a percent by weight particulate material, based on the percent by weight of the non-volatile component and particulate material, such that the coating possesses an L value ranging from 20% (15%, 10%, or even 5%) less or greater than the L value determined by taking the minimum of a first derivative of a curve fit to L value measurements of the coating at different particulate material concentrations.

For instance, as shown in FIG. 7, the L values measured in Example 1 and set forth in Table 1 are plotted at different particle or pigment loadings on a graph, with the L value on the y axis and the particle loading wt % on the x axis. A curve is generated through the L value data using a best fit $5^{th}$ order polynomial (L5). As can be seen from FIG. 7, the curve proceeds through a plateau and the midpoint of the plateau (PV) is identified by determining the L value (L) and particle loading (X) at the minimum of a first derivative of the curve (dL5/dX). The desired L value range is determined such that it is 20% less and greater than PV. That is, $X_{min}$ is the X value where L5=0.8×PV and $X_{max}$ is the X value where L5=1.2×PV. In this example, $X_{min}$ is 13.8 wt % particulate material and $X_{max}$ is 51.5 wt % based on the weight of particulate material and non-volatile component.

Because of the above-described surface morphology of upper surface 24, exemplary film 20 typically exhibits very little intra-film light scattering compared to surface light scattering. In some exemplary embodiments, exemplary film 20 exhibits less than about 50% intra-film light scattering and greater than about 50% surface light scattering based on a total amount of light scattering of exemplary film 20. In other exemplary embodiments, exemplary film 20 exhibits less than about 30% (or less than about 25%, or less than about 20%, or less than about 15%, or less than about 10%, or less than about 5%, or less than about 4%, or less than about 3%, or less than about 2%, or even less than about 1%) intra-film light scattering and greater than about 70% (or greater than about 75%, or greater than about 80%, or greater than about 85%, or greater than about 90%, or greater than about 95%, or greater than about 99%) surface light scattering based on a total amount of light scattering of exemplary film 20.

In addition to having the above-mentioned surface roughness, exemplary film 20 has a desired degree of transparency. Desirably, exemplary film 20 has a desired degree of transparency that enables visual observation of color and tone of a substrate surface (e.g., a skin surface) positioned below exemplary film 20 even when exemplary film 20 has a film thickness of up to about 200 μm. For example, when exemplary film 20 is coated onto skin at a coating thickness of up to about 100 μm, the transparency of exemplary film 20 enables one to visually observe skin color and tone through exemplary film 20. Further, the transparency and composition of exemplary film 20 does not alter the appearance of skin through exemplary film 20 (i.e., skin coated or treated with exemplary film 20 appears substantially identical to untreated skin).

Due to the above-mentioned surface roughness, exemplary film 20 also has a desired degree of obscuring capacity that hides surface imperfections in a substrate surface (e.g., a skin surface) positioned below exemplary film 20 even when exemplary film 20 has a film thickness of as low as about 1 μm. It is believed that the superior obscuration properties of the disclosed films is, at least in part, a result of significant surface light scattering of exemplary film 20 instead of intra-film light scattering.

II. Methods of Making Compositions, Coatings, and Coated Substrates

The present invention is also directed to methods of making compositions capable of obscuring surface imperfections. In one exemplary embodiment, the method of making a coating composition comprises forming a mixture including particulate material and a fluid phase including a non-volatile component, and a volatile component; wherein the coating composition, after being dried on a substrate to form a coating, includes a percent particulate material, based on the percent by weight of the non-volatile component and particulate material, such that the coating possesses an optical performance ratio ranging from within 30% (or 25%, 20%, 15%, 10%, or even 5%) of the maximum optical performance ratio of a curve fit to optical performance ratio measurements of the coating at different particulate material concentrations. This exemplary embodiment produces coatings that possess superior obscuration properties, as well as a desired degree of outermost surface roughness and transparency on a substrate (e.g., skin).

In another exemplary embodiment, the method of making a coating composition comprises forming a mixture including particulate material and a fluid phase including a non-volatile component, and a volatile component; wherein the coating composition includes percent particulate material such that the coating possesses an optical performance ratio of at least about 4.0 (or 4.5, 5.0, 5.5 or even 6.0). This exemplary embodiment produces coatings that possess superior obscuration properties, as well as a desired degree of outermost surface roughness and transparency on a substrate (e.g., skin).

In a further exemplary embodiment, the method of making a coating composition comprises forming a mixture including particulate material and a fluid phase including a non-volatile component, and a volatile component; wherein the coating composition, after being dried on the substrate to form a coating, includes a percent by weight of particulate material, based on the percent by weight of the non-volatile component and particulate material, such that the coating possesses a porosity ranging from 30% (or 25%, 20%, 15%, 10%, or even 5%) less or greater than the porosity determined by taking the minimum of a first derivative of a curve fit to porosity measurements of the coating at different particulate material concentrations. The method of making a composition may further comprise incorporating one or more additional components into the mixture, wherein the one or more additional components include, but are not limited to, deionized water, a humectant, an emollient, a fragrance, or any combination thereof.

In an even further exemplary embodiment, the method of making a coating composition comprises forming a mixture including particulate material and a fluid phase including a non-volatile component, and a volatile component; wherein the coating composition, after being dried on the substrate to form a coating, includes a percent by weight particulate material, based on the percent by weight of the non-volatile component and particulate material, such that the coating possesses an L value ranging from 20% (or 15%, 10%, or even 5%) less or greater than the L value determined by taking the minimum of a first derivative of a curve fit to L value measurements of the coating at different particulate material concentrations. The method of making a composition may further comprise incorporating one or more additional components into the mixture, wherein the one or more additional components include, but are not limited to, deionized water, a humectant, an emollient, a fragrance, or any combination thereof.

The methods of making a composition may further comprise one or more additional steps including, but not limited to, incorporating one or more of the above-mentioned additional components into the mixture; mixing the particulate material, the fluid phase and any optional additional components at room temperature; heating the fluid phase (e.g., to a temperature of less than about 100° C.) while adding one or more components to the fluid phase; and packaging the resulting composition in a sealable container (e.g., a sealable jar, a plastic bottle, or a resealable bag).

In one desired embodiment, the method of making a composition comprises forming a skin care composition specifically formulated for application onto the skin of a human.

The present invention is also directed to methods of forming a coating and methods of forming coated substrates and multi-layer articles. In one exemplary embodiment, a method of forming a coating is disclosed, wherein the method comprises applying any of the above-described compositions onto a substrate. The resulting coated substrate comprises a substrate that is at least partially coated with a suspension or film as described above. The method of forming a coating may further comprise one or more steps including, but not limited to, priming (e.g., washing) the substrate prior to applying the composition.

The methods of forming a coated substrate or multi-layer article may further comprise one or more additional process steps. Suitable additional process steps include, but are not limited to, removing a spreadable/coatable composition from a container, spreading the composition onto the substrate so as to form a film of composition having a desirable film thickness of less than about 200 μm, and repeating any of the above-mentioned steps.

III. Applications/Uses

As discussed above, the compositions of the present invention may be utilized to form coatings on a substrate. Suitable substrates include those where substrate surface defects or imperfections are desirably concealed but still require observation of the substrate surface color and tone. Such substrates include, but are not limited to, cutaneous substrates (e.g., skin), keratinous substrates (e.g., hair, nails, etc.), and even inanimate substrates. In one exemplary embodiment, the compositions of the present invention are used to form a cosmetic treatment over the skin of a human so as to obscure skin imperfections, while showing the natural skin color and tone through the resulting cosmetic treatment. The compositions may be used for daily skin treatment.

The present invention is further directed to methods of using the compositions of the present invention. In one exemplary embodiment, the method of using the composition of the present invention comprises a method of forming a coating on a substrate, wherein the method comprises coating at least a portion of the substrate with a composition including a coating composition including particulate material and a fluid phase including a non-volatile component and a volatile component; wherein the coating composition, after being dried on a substrate to form a coating, includes a percent particulate material, based on the percent by weight of the non-volatile component and particulate material, such that the coating possesses an optical performance ratio ranging from within 30% (or 25%, 20%, 15%, 10%, or even 5%) of the maximum optical performance ratio of a curve fit to optical performance ratio measurements of the coating at different particulate material concentrations. This exemplary embodiment produces coatings that possess superior obscuration properties, as well as a desired degree of outermost surface roughness and transparency on a substrate (e.g., skin).

In another exemplary embodiment, the method of using the composition of the present invention comprises a method of forming a coating on a substrate, wherein the method comprises coating at least a portion of the substrate with a composition including a coating composition including particulate material and a fluid phase including a non-volatile component and a volatile component; wherein the coating composition includes percent particulate material such that the coating possesses an optical performance ratio of at least about 4.0 (or 4.5, 5.0, 5.5, or even 6.0). This exemplary embodiment produces coatings that possess superior obscuration properties, as well as a desired degree of outermost surface roughness and transparency on a substrate (e.g., skin).

In a further exemplary embodiment, the method of using the composition of the present invention comprises a method of forming a coating on a substrate, wherein the method comprises coating at least a portion of the substrate with a composition including a coating composition including particulate material and a fluid phase including a non-volatile component and a volatile component; wherein the coating composition, after being dried on the substrate to form a coating, includes a percent by weight of particulate material, based on the percent by weight of the non-volatile component and particulate material, such that the coating possesses a porosity ranging from 30% (or 25%, 20%, 15%, 10%, or even 5%) less or greater than the porosity determined by taking the minimum of a first derivative of a curve fit to porosity measurements of the coating at different particulate material concentrations. The substrate may comprise a variety of animate and inanimate substrates including, but not limited to, skin.

In an even further exemplary embodiment, the method of using the composition of the present invention comprises a method of forming a coating on a substrate, wherein the method comprises coating at least a portion of the substrate with a composition including a coating composition including particulate material and a fluid phase including a non-volatile component and a volatile component; wherein the coating composition, after being dried on the substrate to form a coating, includes a percent by weight particulate material, based on the percent by weight of the non-volatile component and particulate material, such that the coating possesses an L value ranging from 20% (or 15%, 10%, or even 5%) less or greater than the L value determined by taking the minimum of a first derivative of a curve fit to L value measurements of the coating at different particulate material concentrations. The method may further comprise incorporating one or more additional components into the composition, wherein the one or more additional components include, but are not limited to, deionized water, a humectant, an emollient, a fragrance, or any combination thereof.

The present invention is further directed to multi-layer articles comprising a substrate and the composition of the present invention on an outer surface of the substrate. In one exemplary embodiment, the multi-layer article comprises skin having an outer skin surface; and the herein disclosed obscuring composition on the outer skin surface. The dispersion may include various other components and/or be utilized in other formulations depending upon the desired application. For example, if the composition is intended for use in coating formulations, the composition may be added to the formulation as powder, dispersion, or paste. The compositions may be utilized in cosmetic formulations such as in creams, powders, or pastes.

EXAMPLES

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Test Methods

The following test methods were used in the examples below.

Determination of Non-Volatile Content

For a given fluid, the fluid was weighed, and then heating at 60° C. for 1 hour. Percent of non-volatile content (% NVC) was calculated using the formula:

$$\% \text{ NVC} = [(W_o - W_f) \times 100]/W_o$$

wherein $W_o$ represents the original weight of the fluid, and $W_f$ represents the final weight of the fluid after the heating step.

Determination of Coating Porosity

The porosity of films deposited on glass substrates are measured according to ASTM D6583-04.

Determination of Coating Optical Properties

The optical properties of films formed on glass slides were measured, at 550 nm, using a Shimadzu UV-2401PC UV-VIS spectrophotometer equipped with an Integrating Sphere. The % Diffuse Transmission to Total value is calculated by using the formula: 100× (Diffuse Transmission/Total Transmission). The optical performance ratio (OPR)=Diffuse Transmission/Total Reflection. Higher OPR values indicate a film or coating with high obscuration but with the added ability to allow the underlying substrate color to show. Low OPR values indicate a film or coating with low obscuration at low pigment or particulate material loadings and excessive opacity at high pigment or particulate material loadings.

Determination of Glossiness of Coating

A given coating was visually observed at approximately 60° from a normal angle to an upper surface of the coating. As used herein, the term "Rough" equals low reflectivity, while the term "Glossy" equals high reflectivity (i.e., shiny).

Determination of Opacity of Coating

A given coating was visually observed at approximately 0° from a normal angle to an upper surface of the coating. As used herein, the term "Opaque" equals substantial hiding of the skin, while "Transparent" equals skin color/tone is seen essentially unaffected by coating. The opacity of a film was evaluated as follows: the coated glass slide was placed on top of a Plain Black Chart from Leneta Co. The black color of this chart had a L value of 0.09 (based on the L*a*b* color system) as measured with a Konica Minolta spectrophotometer CM-2600d. Then the L value of the chart was measured through the coated glass slide. The opacity of the films were evaluated based on the measured L values. The L values of transparent films will be lower than those of opaque films.

Determination of Obscuration of Coating

A given coating was visually observed at approximately 0° from a normal angle to an upper surface of the coating. As used herein, the term "Obscuration" equals poor resolution of underlying skin features (e.g., small wrinkles, dark spots freckles, etc.) compared to uncoated skin.

Determination of Resolution of Coating

The resolution of films was evaluated by placing a coated glass slide on top of a Rit Alphanumeric Resolution Test Object, RT-4-74 (Graphic Arts Research Center). The chart has characters printed at different sizes. Each size is identified by a number. Higher numbers correspond to a smaller print size. A film is rated according to the ability of an observer to correctly identify the printed characters through the test film. The corresponding identification number for the first not discernable line of characters is reported. The distance between the film and the chart was 4.8 mm.

Determination of Coating Surface Roughness

The Surface Roughness of a film (Ra) was measured with Zygo NewView 5000 Optical Profilometer. Higher Ra values indicate a rougher surface.

Determination of Non-Volatile Content for Various Fluids

Using the above-described method, the weight percent of non-volatile content (% NVC) was calculated for several fluids. The results are shown in Table 1 below.

TABLE 1

| Fluid | Source | % NVC |
| --- | --- | --- |
| Mineral oil, White Heavy | Mallinckrodt Chemicals (Phillipsburg, NJ) | 100% |
| DOW CORNING ® 245 | Dow Corning Corporation (Midland, MI) | 0% |
| DOW CORNING ® 5329 | Dow Corning Corporation (Midland, MI) | 97% |
| DOW CORNING ® 5200 | Dow Corning Corporation (Midland, MI) | 90% |

Example 1

Performance of Coating Formulations Using Polymeric Binder

The performance of sample formulations shown in Table 2 below was evaluated by applying a small amount of a given coating formulation onto a glass substrate, allowing the coating formulation to dry, and then evaluating the resulting coating. The properties of the coating or film were evaluated in terms of (i) porosity, (ii) opacity, (iii) optical performance ratio, (iv) film surface roughness, and (v) resolution using the above-described test methods.

Silica gel is prepared according to the process disclosed in U.S. Pat. No. 6,380,265 by mixing an aqueous solution of an alkali metal silicate (e.g., sodium silicate) with a strong acid such as nitric or sulfuric acid, the mixing being done under suitable conditions of agitation to form a clear silica sol which sets into a hydrogel, i.e., macrogel, in less than about one-half hour. The resulting gel is then washed. The concentration of inorganic oxide, i.e., $SiO_2$, formed in the hydrogel is usually in the range of about 10 and about 50 weight percent, with the pH of that gel being from about 1 to about 9, preferably 1 to about 4. A wide range of mixing temperatures can be employed, this range being typically from about 20 to about 50° C. The newly formed hydrogels are washed simply by immersion in a continuously moving stream of water which leaches out the undesirable salts, leaving about 99.5 weight percent or more pure inorganic oxide behind. The pH, temperature, and duration of the wash water will influence the physical properties of the silica, such as surface area (SA) and pore volume (PV). Silica gel washed at 65-90° C. at pH's of 8-9 for 15-36 hours will usually have SA's of 250-400 and form aerogels with PV's of 1.4 to 1.7 cc/gm. Silica gel washed at pH's of 3-5 at 50-65° C. for 15-25 hours will have SA's of 700-850 and form aerogels with PV's of 0.6-1.3. The silica has a particle size of 6.4 microns.

The pigment or particulate material is dispersed in water and an appropriate amount of PVOH binder (Celvol-502 available from Celanese Chemicals, 35% solution in water) is added with stirring in order to obtain the desired pigment/particulate material to binder ratios (by weight). The total solids (particulate material and binder) in the formulation were 15 wt % based on the total weight of the formulation. The coating formulation was then applied on a glass slide with a wire-wound bar at a 50 micron wet film thickness and dried under a gentle stream of warm air, and then further dried at 80° C. for 10 minutes. The amount of silica is varied from 5 to 75 wt %, based on the weight of the final film or coating.

TABLE 2

Sample Coating Formulations

| Sample No. | Amount Pigment (wt %) | L Value | Diffuse Transmission | Total Reflection | Optical Performance Ratio | Porosity (%) | Surface Roughness (microns) | Resolution |
|---|---|---|---|---|---|---|---|---|
| 1 | 5 | 9.3 | 8 | 7 | 1.15 | 6 | 0.32 | 13.0 |
| 2 | 10 | 22.9 | 16 | 7 | 2.21 | 9 | 0.40 | 13.0 |
| 3 | 23 | 35.9 | 40 | 8 | 5.39 | 13 | 0.88 | 5.8 |
| 4 | 33 | 37.4 | 47 | 8 | 6.12 | 12 | 1.48 | 0.0 |
| 5 | 46 | 39.7 | 53 | 9 | 6.08 | 14 | 1.68 | −4.5 |
| 6 | 56 | 48.9 | 55 | 16 | 3.38 | 20 | — | −8.3 |
| 7 | 66 | 57.2 | 55 | 25 | 2.22 | 31 | — | −12.0 |
| 8 | 75 | 64.1 | 50 | 36 | 1.39 | 40 | — | −12.0 |

As shown in Table 2, Sample 1 contained a small amount of particulate material added. The resulting film possessed a low optical performance ratio (OPR), and a low L value, which did not provide a desired degree of reduced resolution.

Samples 2-6 provided sample formulations with an increasing amount of particulate material, which resulted in an increased OPR. With an OPR in this range, the resulting films exhibited all of the desirable characteristics, namely, a rough, transparent appearance that provided the desired degree of obscuration.

Samples 7-8 describe provided sample formulations with an increasing amount of particulate material, which resulted in a decreased OPR and increased L value. With an L value in this range, the resulting films exhibited excessive opacity.

Example 2

Performance of Coating Formulations Using Polymeric Binder

The performance of sample formulations shown in Table 3 below was evaluated by applying a small amount of a given coating formulation onto a glass substrate, allowing the coating formulation to dry, and then evaluating the resulting coating. The properties of the coating or film were evaluated in terms of (i) porosity, (ii) opacity, (iii) optical performance ratio, (iv) film surface roughness, and (v) resolution using the above-described test methods.

The pigment or particulate material is dispersed in water and an appropriate amount of PVOH binder (Celvol-502 available from Celanese Chemicals, 35% solution in water) is added with stirring in order to obtain the desired pigment/particulate material to binder ratios (by weight). The total solids (particulate material and binder) in the formulation were 15 wt % based on the total weight of the formulation. The coating formulation was then applied on a glass slide with a wire-wound bar at a 50 micron wet film thickness and dried under a gentle stream of warm air, and then further dried at 80° C. for 10 minutes. The pigment utilized in these sample formulations is a silica gel having a particle size of 2.7 microns, and is made by the process set forth in Example 1. The amount of silica is varied from 5 to 75 wt %, based on the weight of the final film or coating.

TABLE 3

Sample Coating Formulations

| Sample No. | Amount Pigment (wt %) | L Value | Diffuse Transmission | Total Reflection | Optical Performance Ratio | Porosity (%) | Surface Roughness (microns) | Resolution |
|---|---|---|---|---|---|---|---|---|
| 9 | 5 | 4.6 | 5 | 7 | 0.70 | 5 | 0.12 | 13.0 |
| 10 | 10 | 21.2 | 12 | 7 | 1.70 | 6 | 0.22 | 13.0 |
| 11 | 23 | 36.2 | 45 | 8 | 5.91 | 11 | 0.49 | 4.0 |
| 12 | 33 | 38.6 | 56 | 8 | 7.23 | 10 | 0.82 | −3.3 |
| 13 | 46 | 45.6 | 56 | 12 | 4.58 | 11 | 0.88 | −7.3 |
| 14 | 56 | 62.1 | 50 | 35 | 1.44 | 30 | — | −12.0 |
| 15 | 66 | 67.9 | 40 | 49 | 0.81 | 36 | — | −12.0 |
| 16 | 75 | 75.1 | 42 | 47 | 0.88 | 43 | — | −12.0 |

As shown in Table 3, Samples 9 and 10 contain a small amount of particulate material added. The resulting films possess a low optical performance ratio (OPR), and a low L value, which did not provide a desired degree of reduced resolution.

Samples 11-13 provided sample formulations with an increasing amount of particulate material, which resulted in an increased OPR. With an OPR in this range, the resulting films exhibited all of the desirable characteristics, namely, a rough, transparent appearance that provided the desired degree of obscuration.

Samples 14-16 describe provided sample formulations with an increasing amount of particulate material, which resulted in a decreased OPR and increased L value. With an L value in this range, the resulting films exhibited undesirable opacity.

Example 3

Performance of Coating Formulations Using Polymeric Binder

The performance of sample formulations shown in Table 4 below was evaluated by applying a small amount of a given coating formulation onto a glass substrate, allowing the coating formulation to dry, and then evaluating the resulting coating. The properties of the coating or film were evaluated in terms of (i) diffuse transmission, (ii) total transmission, and (iii) % diffuse transmission to total transmission using the above-described test methods.

The pigment or particulate material is dispersed in water and an appropriate amount of PVOH binder having a refractive index of 1.49 to 1.53 (Celvol-502 available from Celanese Chemicals, 35% solution in water) is added with stirring in order to obtain the desired pigment/particulate material to binder ratios (by weight). Two particulate materials were evaluated, silica (refractive index of 1.46 and titania (refractive index of 2.5). The total solids (particulate material and binder) in the formulation were 15 wt % based on the total weight of the formulation. The coating formulation was then applied on a glass slide with a wire-wound bar at a 50 micron wet film thickness and dried under a gentle stream of warm air, and then further dried at 80° C. for 10 minutes. The pigment utilized in these sample formulations 17-22 is a silica gel having a particle size of 6.4 microns, and is made by the process set forth in Example 1. The pigment utilized in these sample formulations 23-29 is a titania in anatase form having a particle size of 0.4 microns, and is available from Sigma Aldrich.

TABLE 4

Sample Coating Formulations

| Sample No. | Pigment Type | Diffuse Transmission | Total Transmission | % Diffuse Transmission to Total | Wet Film Thickness (micron) |
|---|---|---|---|---|---|
| 17 | Silica | 55 | 77.2 | 71 | 24 |
| 18 | Silica | 56.9 | 80.9 | 70 | 40 |
| 19 | Silica | 57 | 80.6 | 71 | 50 |
| 20 | Silica | 56.9 | 79.9 | 71 | 60 |
| 21 | Silica | 55.8 | 83.3 | 67 | 80 |
| 22 | Silica | 59.5 | 89.9 | 66 | 100 |
| 23 | Titania | 34.8 | 69.6 | 50 | 12 |
| 24 | Titania | 42.3 | 57.2 | 74 | 24 |
| 25 | Titania | 42.0 | 45.9 | 92 | 40 |
| 26 | Titania | 39.2 | 40.6 | 97 | 50 |
| 27 | Titania | 32.0 | 32.7 | 98 | 60 |
| 28 | Titania | 29.7 | 30.2 | 98 | 80 |
| 29 | Titania | 24.2 | 24.6 | 98 | 100 |

Based on the similarity of the RI between silica and PVOH, the intra-film scattering is expected to be minimal. The opposite is true for the anatase containing films where the large RI mismatch leads to intra-film scattering.

Optical analyses for this system with substantial intra-film scattering (large RI difference between particle and binder) show a significant decrease in total transmission (and associated increase in opacity) with increasing film thickness. By contrast the first case shows results for similarly prepared samples made using silica gel particles (RI=1.46). In this case there is minimal intra-film scattering (very small difference between particle and binder RI) but significant scattering at the film surface (as indicated in the % diffuse transmission to total values) due to its roughness. This film has the desirable properties of minimal variation with film thickness for both total transmission and % diffuse transmission to total values. As such product of this type would desirably give a very uniform appearance (both in obscuration and reflectance) to the skin even if the application thickness is not particularly uniform.

Example 4

Performance of Coating Formulations Containing Various Concentrations of Particulate Material The performance of sample formulations shown in Table 5 below was evaluated by applying a small amount of a given coating formulation onto skin, allowing the coating formulation to dry for a drying period of 15 minutes, and then evaluating the resulting coating. The appearance of the treated skin area was evaluated in terms of (i) glossiness, (ii) opacity, and (iii) obscuration using the above-described test methods.

Silica from Example 1 is dispersed in 72.5 g of deionized (DI) water using a homogenizer. Then, a fluid phase was added to the DI water/silica mixture and homogenized for 2-3 minutes, followed by the addition of SEPIGEL™ 305 (commercially available from Southern Soapers (Hampton, Va.)).

Each fluid phase was prepared by mixing one or more of: DOW CORNING® 245 Fluid, mineral oil (White Heavy), DOW CORNING® 5329 and DOW CORNING® 5200. The total concentration of silica each mixture remained the same. The weight of the fluid phase remained constant, but the concentration of non-volatile component (NVC) was varied in order to determine the effect of NVC on performance.

TABLE 5

Sample Coating Formulations

| Composition Component | Sample 30 | Sample 31 | Sample 32 | Sample 33 | Sample 34 |
|---|---|---|---|---|---|
| DOW CORNING ® 245 Fluid | 32 | 25.6 | 22.4 | 19.2 | 9.6 |
| Mineral Fluid, White Heavy | 0 | 6.4 | 9.6 | 12.8 | 22.4 |
| DOW CORNING ® 5329 | 4 | 4 | 4 | 4 | 4 |
| Silica Powder | 4 | 4 | 4 | 4 | 4 |
| DOW CORNING ® 5200 Formulation Aid | 0.5 | 0.5 | 0.5 | 0.5 | 0.5 |
| Deionized Water | 72.5 | 72.5 | 72.5 | 72.5 | 72.5 |
| SEPIGEL ™ 305 | 0.6 | 0.6 | 0.6 | 0.6 | 0.6 |
| Total non-volatile component (g) | 4.7 | 11.1 | 14.3 | 17.5 | 27.1 |
| % Silica Powder in dried coating | 46 | 26 | 22 | 19 | 13 |

TABLE 5-continued

Sample Coating Formulations

| Composition Component | Sample 30 | Sample 31 | Sample 32 | Sample 33 | Sample 34 |
|---|---|---|---|---|---|
| Glossiness | Rough | Rough | Rough | Rough | Glossy |
| Opacity | Opaque | Transparent | Transparent | Transparent | Transparent |
| Obscuration | Yes | Yes | Yes | Yes | None |

Sample 30, which includes a small amount of particulate material as a percentage of the total weight of particulate material and NVC, resulted in films that are rough and opaque.

Samples 31-33 provided sample formulations with an increasing amount of NVC. The resulting films exhibited all of the desirable characteristics of a cosmetic cream after 15 minutes, namely, a rough, transparent appearance that obscured the underlying skin features.

Sample 34 provides sample formulations with an increasing amount of NVC, which resulted in films exhibited undesirable glossiness after 15 minutes.

While the invention has been described with a limited number of embodiments, these specific embodiments are not intended to limit the scope of the invention as otherwise described and claimed herein. It may be evident to those of ordinary skill in the art upon review of the exemplary embodiments herein that further modifications, equivalents, and variations are possible. All parts and percentages in the examples, as well as in the remainder of the specification, are by weight unless otherwise specified. Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit, $R_L$, and an upper limit $R_U$, is disclosed, any number R falling within the range is specifically disclosed. In particular, the following numbers R within the range are specifically disclosed: $R=R_L+k(R_U-R_L)$, where k is a variable ranging from 1% to 100% with a 1% increment, e.g., k is 1%, 2%, 3%, 4%, 5% . . . 50%, 51%, 52% . . . 95%, 96%, 97%, 98%, 99%, or 100%. Moreover, any numerical range represented by any two values of R, as calculated above is also specifically disclosed. Any modifications of the invention, in addition to those shown and described herein, will become apparent to those skilled in the art from the foregoing description and accompanying drawings. Such modifications are intended to fall within the scope of the appended claims. All publications cited herein are incorporated by reference in their entirety.

What is claimed is:

1. A composition comprising:
   particulate material having a particulate material refractive index ranging from about 1.2 to about 1.8, said particulate material consisting of alumina, boron nitride, or silica particles, said particulate material being precipitated particles or gel particles; and
   a fluid phase in an amount of from about 10.0 wt % to about 98.0 wt % based on a total weight of the composition, said fluid phase comprising:
   from about 1.0 wt % to about 60 wt % of at least one non-volatile fluid component, based on a total weight of the fluid phase, said at least one non-volatile fluid component having a non-volatile fluid component refractive index ranging from about 1.2 to about 1.8, and
   from about 99.0 wt % to about 40 wt % of at least one volatile fluid component based on a total weight of the fluid phase;
   wherein the composition, after being dried on a substrate, forms a continuous, transparent film (a) that exhibits less than 50% intra-film light scattering and greater than about 50% surface light scattering based on a total amount of light scattering by the film, and (b) has an optical performance ratio of at least 4.0.

2. The composition of claim 1, wherein said particulate material consists of precipitated silica particles or silica gel particles.

3. The composition of claim 1, wherein said optical performance ratio is at least about 4.5.

4. A dried film formed from the composition of claim 1.

5. The dried film of claim 4, wherein said dried film comprises a transparent continuous film having an outermost rough surface.

6. The dried film of claim 5, wherein said dried film comprises from about 19 wt % to about 26 wt % of total particulate material based on a total weight of (i) all particulate material and (ii) said at least one non-volatile fluid component within the continuous, transparent film.

7. A method of hiding skin imperfections, said method comprising:
   applying the composition of claim 1 onto an outer skin surface.

8. The composition of claim 1, wherein a given optical performance ratio comprises a ratio of (i) a diffusion transmission value divided by (ii) a total reflection value for a given composition.

9. The composition of claim 1, wherein said particulate material consists of precipitated silica particles or silica gel particles; said at least one non-volatile fluid component comprises one or more components selected from oils, waxes, glycerin, and any combination thereof; and said at least one volatile fluid component comprises one or more components selected from silicones, deionized water, solvents, fragrances, and any combination thereof.

10. The composition of claim 1, wherein said particulate material has a particulate material refractive index ranging from about 1.4 to about 1.6, and said at least one non-volatile fluid component has a non-volatile fluid component refractive index ranging from about 1.4 to about 1.6.

11. The composition of claim 1, wherein the composition, after being dried on a substrate, forms a continuous, transparent film that exhibits less than 25% intra-film light scattering and greater than about 75% surface light scattering based on a total amount of light scattering by the film.

12. The composition of claim 1, wherein the composition, after being dried on a substrate, forms a continuous, transparent film that comprises from about 19 wt % to about 26 wt % of total particulate material based on a total weight of (i) all particulate material and (ii) said at least one non-volatile fluid component within the continuous, transparent film.

13. The composition of claim 1, wherein said composition consists of said particulate material and said fluid phase.

14. The composition of claim 1, wherein (1) said particulate material consists of precipitated silica particles or silica gel particles, and (2) said fluid phase comprises from about 1.0 wt % to about 40.0 wt % of said at least one non-volatile fluid component, based on a total weight of the fluid phase, and from about 99.0 wt % to about 60.0 wt % of said at least one volatile fluid component based on a total weight of the fluid phase.

15. A transparent coating for hiding skin imperfections, said transparent coating comprising:
   particulate material having a particulate material refractive index ranging from about 1.2 to about 1.8, said particulate material consisting of alumina, boron nitride, or silica particles, said particulate material being precipitated particles or gel particles; and
   a fluid phase in an amount of from about 10.0 wt % to about 98.0 wt % based on a total weight of the composition, said fluid phase comprising:
      from about 1.0 wt % to about 60.0 wt % of at least one non-volatile fluid component, based on a total weight of the fluid phase, said at least one non-volatile fluid component having a non-volatile fluid component refractive index ranging from about 1.2 to about 1.8, and
      from about 99.0 wt % to about 40.0 wt % of at least one volatile fluid component based on a total weight of the fluid phase;
   wherein the transparent coating, after being dried on a substrate, forms a continuous, transparent film (a) that exhibits less than 50% intra-film light scattering and greater than about 50% surface light scattering based on a total amount of light scattering by the film, and (b) has an optical performance ratio of at least 4.0.

16. The transparent coating of claim 15, wherein said particulate material has a particulate material refractive index ranging from about 1.4 to about 1.6, and said at least one non-volatile fluid component has a non-volatile fluid component refractive index ranging from about 1.4 to about 1.6.

17. The transparent coating of claim 15, wherein the transparent coating, after being dried on a substrate, forms a continuous, transparent film that exhibits less than 25% intra-film light scattering and greater than about 75% surface light scattering based on a total amount of light scattering by the film.

18. The transparent coating of claim 15, wherein the transparent coating, after being dried on a substrate, forms a continuous, transparent film that comprises from about 19 wt % to about 26 wt % of total particulate material based on a total weight of (i) all particulate material and (ii) said at least one non-volatile fluid component within the continuous, transparent film.

19. The transparent coating of claim 15, wherein (1) said particulate material consists of precipitated silica particles or silica gel particles, and (2) said fluid phase comprises from about 1.0 wt % to about 40.0 wt % of said at least one non-volatile fluid component, based on a total weight of the fluid phase, and from about 99.0 wt % to about 60.0 wt % of said at least one volatile fluid component based on a total weight of the fluid phase.

* * * * *